(12) United States Patent
Van Der Graaf

(10) Patent No.: US 10,596,291 B2
(45) Date of Patent: Mar. 24, 2020

(54) EFFECTIVE ANTI-BACTERIA AND ANTI-VIRAL AIR TREATMENT DEVICE

(71) Applicant: KONINKLIJKE PHILIPS N.V., Eindhoven (NL)

(72) Inventor: Timothy Van Der Graaf, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 208 days.

(21) Appl. No.: 15/538,726

(22) PCT Filed: Dec. 21, 2015

(86) PCT No.: PCT/EP2015/080812
§ 371 (c)(1),
(2) Date: Jun. 22, 2017

(87) PCT Pub. No.: WO2016/102478
PCT Pub. Date: Jun. 30, 2016

(65) Prior Publication Data
US 2019/0105421 A1 Apr. 11, 2019

(30) Foreign Application Priority Data
Dec. 23, 2014 (EP) .................................... 14200104

(51) Int. Cl.
A61L 9/22 (2006.01)
A61L 9/04 (2006.01)
(Continued)

(52) U.S. Cl.
CPC ............... *A61L 9/032* (2013.01); *A61L 9/122* (2013.01); *A61L 2202/25* (2013.01);
(Continued)

(58) Field of Classification Search
CPC ..... A61L 9/22; A61L 9/04; A61L 9/12; B01D 53/32; B01D 53/8675
(Continued)

(56) References Cited

U.S. PATENT DOCUMENTS 2,608,436 A 8/1952 Leonard
6,312,507 B1 * 11/2001 Taylor .................. A01K 1/0107
119/165
(Continued)

FOREIGN PATENT DOCUMENTS

CH 115858 7/1926
CN 202128731 U 2/2012
(Continued)

OTHER PUBLICATIONS

Calogirou, et al: "Decomposition of Terpenes by Ozone during Sampling on Tenax", Anal. Chem. 1996, 68, 9, 1499-1506, Abstract.
(Continued)

*Primary Examiner* — Monzer R Chorbaji

(57) ABSTRACT

The invention provides an air treatment device (100) configured to deactivate one or more of bacteria and viruses from air, the device (100) comprising a deactivating material (121) comprising for at least 80 wt. % of one or more of a terpene and a terpenoid having no aliphatic unsaturated bond, the air treatment device (100) further comprising a gas flow generation device (130), wherein the air treatment device (100) is configured to provide said deactivating material (121) into a space with an emission rate (S) of at maximum 250 mg/h from a release area (1112).

20 Claims, 5 Drawing Sheets

(51) Int. Cl.
*A61L 9/12* (2006.01)
*B01D 53/32* (2006.01)
*A61L 9/03* (2006.01)

(52) U.S. Cl.
CPC .... *A61L 2209/111* (2013.01); *A61L 2209/133* (2013.01); *A61L 2209/21* (2013.01)

(58) Field of Classification Search
USPC ............... 422/1, 4–5, 28, 120, 306; 261/75; 239/93
See application file for complete search history.

(56) References Cited

U.S. PATENT DOCUMENTS

| | | | |
|---|---|---|---|
| 7,638,114 | B1 | 12/2009 | Schur |
| 8,833,366 | B2 | 9/2014 | Colombo |
| 10,182,589 | B2 | 1/2019 | Lee |
| 2013/0306158 | A1* | 11/2013 | Sardo ............ A01N 3/00 137/10 |

FOREIGN PATENT DOCUMENTS

| | | |
|---|---|---|
| CN | 203139866 U | 8/2013 |
| EP | 355317 A2 | 2/1990 |
| FR | 2790923 | 9/2000 |
| GB | 425309 A | 3/1935 |
| JP | H09225017 | 9/1997 |
| JP | 2000060953 | 2/2000 |
| JP | 2003079713 | 3/2003 |
| KR | 20130054823 A | 5/2013 |
| WO | 2013/128213 | 9/2013 |

OTHER PUBLICATIONS

Institute for Health and Consumer Protection, Physical and Chemical Exposure Unit, 2005 "Critical Appraisal of the Setting and Implementation of Indoor Exposure Limits in the EU the INDEX project".

European Collaborative Action Urban Air, Indoor Environment and Human Exposure, 2007 "Impact of Ozone-initiated Terpene Chemistry on Indoor Air Quality and Human Health".

Inouye, et al: "Antibacterial activity of essential oils and their major constituents against respiratory tract pathogens by gaseous contact", Journal of Antimicrobial Chemotherapy, vol. 47, Issue 5, May 2001, pp. 565-573.

Tunga Salthammer, "Critical evaluation of approaches in selling indoor air quality guidelines and reference values", vol. 82, Issue 11, Mar. 2011, pp. 1507-1517.

Orhan, et al: "Antimicrobial and antiviral effects of essential oils from selected Umbelliferae and Labiatae plants and individual essential oil components" Turkish Journal of Biology, 2012.

Tunga Salthammer, "Formaldehyde in the Ambient Atmosphere: From an Indoor Pollutant to an Outdoor Pollutant?", Angewandte Chemie 2013, Abstract.

Krist, et al: "Effects of scents on airborne microbes, part I: thymol, eugenol, trans-cinnamaldehyde and linalool", 2006 Abstract.

Kloucek, et al: "Fast screening method for assessment of antimicrobial activity of essential oils in vapor phase", Food Research International 47:161-165—Jul. 2012.

Ehrlich, et al: "Relationship Between Atmospheric Temperature and Survival of Airborne Bacteria", Appl Microbiol. Feb. 1970; 19(2): 245-249.

Beko, et al: "Ventilation rates in the bedrooms of 500 Danish children", Building and Environment 45(10):2289-2295—Oct. 2010.

Sato, et al: "Antimicrobial effect of vapours of geraniol, (R)-(–)-linalool, terpineol, γ-terpinene and 1,8-cineole on airborne microbes using an airwasher", 2007, Abstract.

Sato, et al: "Antimicrobial Effect of trans-Cinnamaldehyde, (–)-Perillaldehyde,(–)-Citronellal, Citral, Eugenol and Carvacrol on Airborne Microbes Using an Airwasher", Biol. Pharm. Bull. 29(11) 2292-2294 (2006).

Chinese Indoor Air Quality standard GB 18801-2008, Dec. 30, 2008.

Indoor Air Quality Guidelines and Standards: Final Report 5.1, 2005.

Iwashita, et al "Discussion on the Decrease of SESQUI-Terpenes and the Possibility of Formaldehyde Generation Caused by the Chemical Reaction Between Ozone and SESQUI-Terpenes Emitted From Cedarwood", Journal of Environmental Engineering (Transactions of AIJ) 69(581):53-58—Jul. 2004, Abstract.

* cited by examiner

EFFECTIVE ANTI-BACTERIA AND ANTI-VIRAL AIR TREATMENT DEVICE

This application is the U.S. National Phase application under 35 U.S.C. § 371 of International Application No. PCT/EP2015/080812, filed on Dec. 21, 2015, which claims the benefit of International Application No. 14200104.9 filed on Dec. 23, 2014. These applications are hereby incorporated by reference herein.

FIELD OF THE INVENTION

The invention relates to an air treatment device and to a(n air) treatment system including such air treatment device. The invention further relates to a combination of such air treatment device and a cartridge that can be used in such device, as well as to the cartridge per se. The invention yet further relates to the use of deactivating material to deactivate bacteria and/or viruses in air in a space.

BACKGROUND OF THE INVENTION

The use of terpenes as odorants is known in the art. GB425309, for instance, describes that air in closed spaces, such as theatres, is purified by vaporizing therein a mixture of camphene with menthol and with one or more other terpenes such as pinene and phellandrene, and with or without alcohol. Mixtures specified are (1) menthol and oil of camphor, and (2) menthol, oil of camphor and alcohol. The vapors are introduced into the air at a point where there is an undisturbed upward flow of warm air. Perfumes may be added to the purifying agents.

SUMMARY OF THE INVENTION

The presence of viruses and/or bacteria in air is in general not desired, especially not in e.g. hospitality areas like hospitals, elderly homes, etc. Further, also the presence of undesired chemicals or particles may be undesirable. It appears however that prior art air treatment devices generate too much undesired compounds and/or particles (fine particles). Hence, such prior art air treatment devices may in fact be unhealthy, especially when such air treatment devices are based on the proliferation of chemical compounds which are unhealthy in the concentrations the chemical compounds are proliferated.

Hence, it is an aspect of the invention to provide an alternative air treatment device, which especially further at least partly obviates one or more of above-described drawbacks. It is also an aspect of the invention to provide an alternative air treatment system, which especially further at least partly obviates one or more of above-described drawbacks. Yet, it is an aspect of the invention to provide an alternative deactivating material for such air treatment device or air treatment system, which especially further at least partly obviates one or more of above-described drawbacks. Yet, it is a further aspect of the invention to provide an alternative air treatment method which especially further at least partly obviates one or more of above-described drawbacks.

In a first aspect, the invention provides an air treatment device (herein also indicated as "device") configured to deactivate one or more of bacteria and viruses from air (in a (closed) space), the device comprising a deactivating material comprising for at least 80 wt. % of one or more of a terpene and a terpenoid having no aliphatic unsaturated bond, the air treatment device further comprising a gas flow generation device ("gas flow device"), wherein the air treatment device is configured to provide said deactivating material into the space with an emission rate (S) of at maximum 250 mg/h from a release area.

It appears that with the specific selection of the deactivating material it may be circumvented that undesired chemical compounds are formed. Further, it appears that the fine particle formation can be lower than in prior art solutions, or even be negligible. Further, with the specific selection of the deactivating material it appears that bacteria and viruses may be inactivated, whereas in prior art solutions this function seemed to be absent. Especially, bio-aerosols containing species such as bacteria and viruses can be treated with the present device and method. Species that were successfully eliminated already in only preliminary tests were e.g. *S. epidermidis* and bacteriophage MS-2 (herein further also indicated as "MS-2" or "MS2"). *Staphylococcus epidermidis* is a Gram-positive bacterium, and is especially a risk for patients with compromised immune systems. Bacteriophage MS2 is an icosahedral, positive-sense single-stranded RNA virus, and may also be a risk for people. With the present invention, other airborne bacteria and/or viruses frequently found indoors may effectively be deactivated as well. Hence, in this way the device can treat the air in a space and provide a healthier atmosphere in the space. A concentration of the deactivation material is introduced in the air in such space, leading to the deactivation of biological species like viruses and/or bacteria (in such space), without (substantial) introduction of undesired amounts or undesired conversion products or fine particles, thereby improving the quality of said air in said space.

The air treatment device comprises amongst others a gas flow generation device, herein also indicated as gas flow generator or gas flow generator device. This gas flow generation device provides a flow of air in a space where the air treatment device is arranged or to which the air treatment device provides said deactivating material. As will be understood by a person skilled in the art, the device may be arranged in such space, but may also be arranged elsewhere but be configured in fluid contact with said space.

The deactivating material may be configured within the device, e.g. within a chamber (see also below), but may optionally also be partly configured at an external part of the device. Due to the fact that the device generates a gas flow, i.e. especially a flow of air in a space, this flow will also entrain some of the deactivating material. The deactivating material is thus especially configured accessible to the flow generated by the gas flow generator and/or (directly) to the air external from the air treatment device.

As indicated above, the deactivating material is especially selected to have at least 80 wt. % of one or more of a terpene and a terpenoid, more especially at least 90 wt. %, yet even more especially at least 95 wt. %, yet even more especially at least 98 wt. %, such as at least 99 wt. %, yet even more especially at least 99.5 wt. % (relative to the total amount of deactivating material) having no aliphatic double bond. The remainder, here at maximum 20 wt. %, at maximum 10 wt. %, and at maximum 5 wt. %, respectively, may include terpenes and terpenoids having double bonds, and optionally other material. The amount of other material, such as impurities, will especially be lower than 5 wt. %, such as lower than 2 wt. %, like lower than 1 wt. %, or even equal to or lower than 0.5 wt. % (relative to the total amount of deactivating material), or may even be negligible. The presence of impurities may depend upon e.g. extraction starting material and the extent of purification, as known in the art. The terms "terpene" and "terpenoid" are known to the person skilled in the art. Terpenes are a large and diverse class of organic compounds, amongst others produced by a variety of plants, particularly conifers and herbs. The difference between terpenes and terpenoids may be defined as that terpenes are hydrocarbons, whereas terpenoids contain additional functional groups. Herein, for the sake of simplicity, the term "terpene" is used and indicates both terpenes and terpenoids, unless indicated otherwise. The deactivating material may thus comprise high purity non-reactive terpenes/terpenoids.

Terpenes may especially be regarded as polymers or derivatives of isoprene (C5H8). Terpenes may include monoterpenes which are especially tested herein, because of their occurrence in many essential oils. Monoterpenes can be cyclic, acyclic (linear), regular or irregular. Their derivatives include ketones, aldehydes, lactones, alcohols, esters, phenols, (other) aromatic double bond containing derivatives, and oxides. Note that the terpenes may include aromatic double bounds, such as phenyl groups.

Due to the selection of substantially saturated aliphatic systems, it surprisingly appears that the amount of undesired conversion products, such as formaldehydes, is substantially lower than when commercially available terpene mixtures are applied. For instance, when "essential oils" are applied, the formaldehyde level appears to become unacceptable high and/or the ultra fine particle level becomes unacceptable high. However, when using the deactivating material as defined herein, acceptable levels or even extremely low levels, well below levels defined by governmental organizations for these species, may be achieved.

As indicated above, the deactivating material may especially be entrained by a gas flow, especially either already within the air treatment device and/or in the gas flow generated in the space. Hence, especially the deactivating material may have a relative low vapor pressure. In a specific embodiment, the deactivating material has a boiling point selected from the range of 150-300° C. or has a boiling point range at least partly overlapping with said range of 150-300° C. When pure terpenes would be used, the deactivating material may have a boiling point, whereas a mixture of two or more terpenes is used, or a mixture of one or more terpenes with another material, a boiling point range may be perceived. In such instance, the boiling point range at least partly, or especially entirely, overlaps with the indicated range of 150-300° C. As indicated above, the deactivating material comprises in a specific embodiment for at least 95 wt. % of one or more of a terpene and a terpenoid having no aliphatic unsaturated bond. By selecting these type of terpenes, also the desired boiling point (range) may be obtained (see also further below for a list of terpenes that may be used).

Especially desired terpenes may be selected from the group consisting of Menthol, Isomenthol, Neomenthol, Neoisomenthol, Menthone, Isomenthone, Eucalyptol (1,8-cineol), 1,4-cineol, m-Cymene, p-Cymene, Carvacrol, Thymol, p-Cymen-8-ol, Cuminaldehyde, Cuminylalcohol, Iridoid, and Seco-iridoid. Especially, the deactivation material comprises for at least 80 of one or more of Menthol, Isomenthol, Neomenthol, Neoisomenthol, Menthone, Isomenthone, Eucalyptol (1,8-cineol), 1,4-cineol, m-Cymene, p-Cymene, Carvacrol, Thymol, p-Cymen-8-ol, Cuminaldehyde, Cuminylalcohol, Iridoid, and Seco-iridoid, more especially at least 90 wt. %, yet even more especially at least 95 wt. %, yet even more especially at least 98 wt. %, such as at least 99 wt. %, yet even more especially at least 99.5 wt. % (relative to the total amount of deactivating material). Especially, the deactivating material comprises one or more of eucalyptol (1,8-cineol) and thymol. Hence, in such embodiment(s), the deactivating material at least comprises one or more of eucalyptol and thymol, such as a mixture of at least 95 wt. % of these terpenes. The remainder may essentially comprise terpenes with aliphatic double bonds.

Especially, the deactivating material comprises monoterpenes. Alternatively or additionally, the deactivating material may comprise a bicyclic-monoterpene, such as one or more of Borneol, Isoborneol, Bornyl acetate, Camphor, Fenchone, Alpha-fenchol, and Beta-fenchol. Alternatively or additionally, the deactivating material may also include another terpene (or terpenoid) that can provide one or more of the above indicated advantages and/or may lead to the below indicated conditions(s). Further terpenes than mentioned herein can e.g. be derived from Terpenes by Eberhard Breitmaier, Wiley-VCH Verlag GmbH & Co. KGaA, 2006, pages 1-118, which is incorporated herein by reference.

The deactivating material may be provided as such, e.g. in a (open) container. Alternatively or additionally, a material impregnated with the deactivating material may be applied. Yet alternatively or additionally, a liquid may be applied wherein the deactivating material may be solved, e.g. in ether, ethanol, (iso-)propanol, and chloroform, especially one or more of ethanol and iso-propanol. For instance, a deactivating material comprising for at least 95 wt. % of eucalyptol and thymol may be mixed with ethanol to provide a liquid. The carrier material, such as a cartridge, an absorbing material, a liquid, etc., is thus not considered as deactivating material. For instance, this might provide a mixture of 30 wt. % deactivating material and 70 wt. % of a carrier or liquid, such as ethanol and/or isopropanol. This may lead to evaporation of both the deactivating material and e.g. the liquid. The deactivating material is especially chosen such, that the deactivating material that is brought into the air has a composition of at least 80 wt. % of terpenes without an aliphatic double bond and at maximum 20 wt. % terpenes with an aliphatic double bond. This may be obtained, when providing deactivating material having the herein indicated composition, i.e. at least 80 wt. %, especially at least 90 wt. %, yet even more especially at least 95 wt. %, such as at least 98 wt. %, such as even more especially at least 99 wt. %, such as especially at least 99.5 wt. %, relative to the total amount of deactivating material comprises terpenes without an aliphatic double bond.

As indicated above, the deactivating material is introduced in a space. This may be the ambient of the device, or it may be a remote space, in fluid connection with the device. The term space may for instance relate to a (part of) hospitality area, such as a restaurant, a hotel, a clinic, or a hospital, etc. The term "space" may also relate to (a part of) an office, a department store, a warehouse, a cinema, a church, a theatre, a library, etc. However, the term "space" also relate to (a part of) a working space in a vehicle, such as a cabin of a truck, a cabin of an air plane, a cabin of a vessel (ship), a cabin of a car, a cabin of a crane, a cabin of an engineering vehicle like a tractor, etc. The term "space" may also relate to (a part of) a working space, such as an office, a (production) plant, a power plant (like a nuclear power plant, a gas power plant, a coal power plant, etc.), etc. For instance, the term "space" may also relate to a control room, a security room, etc. Hence, the term "space" may especially relate to a "closed" space (even though such space may of course include one or more of a door and a window and another opening, as will be clear to a person skilled in the art).

The deactivating material is introduced in this space with the indicated emission rate of at maximum 250 mg/h from a release area. The device may include one or more release areas, such as one or more openings, respectively (see also below). However, the deactivating material is not necessarily entirely enclosed by the air treatment device (see further below), but may also be associated with an external part of the air treatment device. As the air treatment device is configured to generate an air flow in the space, such air flow will further facilitate entrainment and/or distribution of the deactivation material. Note that due to the selection of the deactivation material evaporation only may be used to provide the indicated emission. Especially, evaporation is stimulated or controlled by the gas flow generated by the air treatment device (especially with the gas flow generation device).

Alternatively or additionally, the deactivating material may be one or more of sprayed, nebulized, atomized, etc., especially as indicated above with an emission rate of at maximum 250 mg/h (from a release area, such as a spray outlet, a nebulizer outlet, an atomizer outlet, etc.). The gas flow generation device may especially (further) be used to facilitate distribution of the emitted deactivating material in a space.

Optionally, the deactivation material may be heated with a heater comprised by the air treatment device. This may facilitate evaporation of the deactivation material. The temperature is especially selected within the above indicated temperature range(s), and especially below a possible decomposition temperature of one or more terpenes. Further, such heater can (additionally) be used to control evaporation of (at least part) of the deactivating material.

It may be convenient to provide the deactivating material in such a way, that when the deactivating material gets depleted, new deactivation material can be reintroduced. Hence, especially the device may comprise a deactivating material unit configured to host the deactivating material, wherein the deactivating material unit is configured as refillable unit, and wherein the deactivating material is comprised by a deactivating material cartridge. For instance, the refillable unit may be refilled with the deactivation material. Alternatively, a cartridge comprising the deactivating material may be included in the deactivating material unit, and may when depleted from deactivation material be replaced with a fresh cartridge. The deactivating material unit may be configured dependent upon the way the deactivating material is provided, such as a liquid (mixture), a cartridge containing such liquid (mixture), a powder, a cartridge, or other element comprising material impregnated with the deactivating material, etc.

In a specific embodiment, the air treatment device comprises a device chamber with an inlet opening and an outlet opening, the air treatment device in operation configured to comprise the deactivating material at least partially enclosed by the device chamber, wherein the gas flow generation device is configured to introduce air from the space via the inlet opening into the device chamber and to transport at least part of the deactivating material with the air via the outlet opening into the space, wherein the air treatment device is configured to provide said deactivating material into the space with an emission rate (S) of at maximum 250 mg/h from said outlet opening. By inclusion of the deactivation material in a chamber through which or along which the gas flow propagates, the emission (rate) of the deactivation material may be even better controlled. The gas flow generation device may be included in the chamber or may be configured external from the chamber (but in fluid contact with the chamber).

In a specific embodiment, the inlet opening and outlet opening refer to the same opening. For instance, a large opening may be applied with an inlet section and an outlet section. Alternatively or additionally, the air treatment device may be used in a batch process, wherein through an opening first air is introduced, and subsequently air enriched with the deactivation material is emitted from the device.

The above indicated maximum emission rate 250 mg/h is especially related to a single release area of the air treatment device, such as an opening. Assuming a large space, more release areas may be used, such as more openings. However, especially these are arranged remote from each other and/or the emission rate may be maximized to prevent locally to high concentrations. Especially, see also below, the concentration (in the air) of the deactivating material is below 2 $mg/m^3$, especially below 1 $mg/m^3$, such as below 0.6 $mg/m^3$. In a specific embodiment, the air treatment device may be configured to maintain a concentration of the deactivating material in air in a space at a level selected from the range of 0.001-1 $mg/m^3$. To this end, the device may include one or more sensors. This is further elucidated in relation to the air treatment system.

For smaller rooms, such as offices, rooms in houses or apartments, the emission rate of 250 mg/h may be relatively high. Hence, the air treatment device may be limited at a lower emission value. Alternatively or additionally, the air treatment device may have a controllable emission rate, with values for spaces with different volumes. For instance, the air treatment device may include a user interface with (temporarily) displaying selectable options relating to space size. For instance, symbols can be used for different types of rooms (or spaces), or e.g. the surface area of the space may be used as input value, based on which the air treatment device may select the appropriate emission rate. Hence, in a further aspect the invention provides an air treatment device as defined herein, (further) complying with one or more of the following conditions (i) having a controllable emission rate (S) and (ii) wherein the air treatment device is limited at an emission rate (S) selected from the range of 0.5-50 mg/h from said release area. As indicated above, when there are more release areas, each may be configured to provide the deactivating material at an emission rate (S) selected from the range of 0.5-50 mg/h from the respective release area. Hence, in a further embodiment the air treatment device comprises a plurality of release areas, wherein the air treatment device is configured to provide said deactivating material into the space with said emission rate (S) from each of said release areas.

The gas flow generator can be any generator, such as a pump, a fan, etc., that is able to provide a gas flow. In a specific embodiment, the gas flow generation device comprises an ionic wind generator. In such instance, the ionic wind generator may especially be configured in the vicinity of the deactivating material, even more especially with electric field lines directed to the deactivating material. The term "gas flow generator" may also refer to a plurality of (different types of) gas flow generators.

In an embodiment, the air treatment device further comprises a humidifier. Hence, the air treatment device may further also be configured to humidify the air in said space. Therefore, in an embodiment the air treatment device is configured to enrich air in a space with one or more of deactivating material and water.

In yet a further aspect, the invention provides an air treatment system comprising (i) the air treatment device as defined herein and (ii) a control unit configured to control the emission rate (S) (of the air treatment device). The control unit may be configured to generate a steady gas flow, by which a constant emission rate may be obtained. For instance, in combination with a predefined use, such as defined relative to a certain volume of a room or a volume ranges of rooms, and/or in combination with a controllable emission, such system may be used to provide the required emission to obtain the above indicated effects without introducing too much deactivating material and/or inducing generation or introduction of undesired species. In a specific embodiment, such system may be configured to maintain a concentration of the deactivating material in air in a space at a level selected from the range of 0.001-1 $mg/m^3$, such as in the range of 0.001-0.6 $mg/m^3$, like in the range of 0.05-0.6 $mg/m^3$, like at least 0.1 $mg/m^3$. It appears that with values of about 0.6 $mg/m^3$ or lower, very good results may be obtained in view of deactivation of bacteria and viruses and in terms of fulfilling requirements concerning undesired chemicals like formaldehyde and fine particles. Alternatively or alternatively, the control unit may e.g. be configured to open, close or adjust the dimensions of the opening of the deactivating material unit and/or the inlet and/or the outlet, and/or to adjust the air-flow generated by gas flow generation device.

Optionally, the system may e.g. include a sensor configured to sense the concentration of the deactivating product and/or of one or more conversion products, and/or other parameters like one or more of temperature, pressure, gas flow, humidity, etc. Hence, in a further embodiment of the air treatment system, the system may further comprising a sensor configured to sense one or more of (i) a concentration of a component in air of the deactivating material in a space, (ii) an ultra fine particles concentration in air in a space, (iii) a conversion product concentration (such as a formaldehyde concentration) in a space, and (iv) another physical or chemical parameter in said space, and wherein the control unit is configured to control the emission rate (S) as function of a sensor signal of said sensor and a corresponding predetermined value for one or more of said component, said ultra fine particles, said conversion product, and said physical or chemical parameter. The term "component of deactivating material" especially refers to embodiments wherein the deactivating material comprises two or more components, such as two or more different terpenes.

For instance, the sensor configured to sense another physical or chemical parameter may include a temperature sensor. For instance, such temperature sensor may be configured to measure the ambient temperature, i.e. the temperature in the space (which is served by the treatment device). For instance, the control unit may be configured to control the emission as function of the temperature (as measued by the temperature sensor). In this way, it may e.g. be possible to adjust the treatment device operation to for instance higher emission rates at lower temperatures and/or lower evaporation rates at higher temperatures (as the natural evaporation may then already be higher). For instance, in combination with a heater, the evaporation rate of at least part of the deactivating material can be controlled. Hence, the control unit may also be configured to control the optional heater (which heater is especially configured to (further) facilitate conversion of the deactivating material in the device into the air in the space). The sensor configured to sense another physical or chemical parameter may in yet a further embodiment include sensor configured to sense a compound other than a terpene (including terpenoids), such as a solvent material or a(nother) fragrance material. For instance, when the deactivating material is provided in combination with another liquid, such as a solvent, such sensor may be configured to sense evaporated liquid molecules, etc. Based thereon, the control unit may (further) control the emission rate.

In a further embodiment, the system may include two or more of the air treatment devices. As indicated above, the term "treatment device" may also refer to a plurality of treatment devices. Further, the system may include two or more release areas, such as two or more outlets. Further, the system may be configured to serve two or more different spaces, such as two or more rooms in a building. Further, the system may include one or more other devices that treat the air, such a humidifier. As indicated above, the air treatment device of the invention may optionally also include a humidifier.

In yet a further aspect, the invention provides a kit of parts comprising (i) the air treatment device as defined herein or the air treatment system as defined herein, and (ii) one or more cartridges comprising said deactivating material, especially a plurality of cartridges comprising said deactivating material, wherein the air treatment device comprises a deactivating material unit configured to host the deactivating material, wherein the deactivating material unit is configured as refillable unit configured to host one or more of said cartridges. The optional additional cartridges can be used to refill the deactivating material unit (e.g. configured as "cartridge holder") when the deactivating material is depleted. The term "cartridge" may refer to any unit, cylinder, holder, part that can comprise the deactivating material.

Therefore, in yet a further aspect the invention also provides such cartridge comprising deactivating material for use in the air treatment device as defined herein, wherein the deactivating material comprises for at least 80 wt. % one or more of Menthol, Isomenthol, Neomenthol, Neoisomenthol, Menthone, Isomenthone, Eucalyptol (1,8-cineol), 1,4-cineol, m-Cymene, p-Cymene, Carvacrol, Thymol, p-Cymen-8-ol, Cuminaldehyde, Cuminylalcohol, Iridoid, and Secoiridoid. In a specific embodiment (see also above), the deactivating material comprises for at least 95 wt. % of one or more of said terpenes and terpenoids. Optionally, the cartridge contains a combination of the deactivating material and a liquid, such as a mixture of ethanol and a terpene without an aliphatic double bond. The term "liquid" may also refer to a plurality of liquids.

Therefore, in yet a further aspect the invention also provides a method for deactivating biological species, such as especially one or more of bacteria and viruses from air in a space, by providing deactivating material comprising for at least 80 wt. % of one or more of a terpene and a terpenoid having no aliphatic unsaturated bond, to said space with a concentration of the deactivating material in air in said space at a level selected from the range of 0.001-1 $mg/m^3$. In yet a further aspect, the invention also provides the use of a deactivating material for deactivating one or more of bacteria and viruses from air in a space, the deactivating material comprising for at least 80 wt. % of one or more of a terpene and a terpenoid having no aliphatic unsaturated bond, with a concentration of the deactivating material in air in said space at a level selected from the range of 0.001-1 $mg/m^3$. More especially, this may include providing said deactivating material in a concentration of the deactivating material in air in said space at a level selected from the range of 0.001-0.6 $mg/m^3$, like in the range of 0.05-0.6 $mg/m^3$, like at least 0.1 $mg/m^3$.

As also indicated above, in a specific embodiment said air treatment device as defined herein is used, and the deactivating material comprises one or more of Menthol, Isomenthol, Neomenthol, Neoisomenthol, Menthone, Isomenthone, Eucalyptol (1,8-cineol), 1,4-cineol, m-Cymene, p-Cymene, Carvacrol, Thymol, p-Cymen-8-ol, Cuminaldehyde, Cuminylalcohol, Iridoid, and Seco-iridoid (see also above for further specific embodiments).

In an embodiment, the invention provides a device in which a fan is replaced by an ionic wind module. In yet a further embodiment, a device is provided in which the fan is placed between the active material enclosure and the outlet. In a further embodiment, a device is provided which also contains other components like particle filters, gas filters (such as activated carbon filters), ionizers, UV-lamps, Photocatalytic devices, plasma generating modules, water tank, humidifying module, dehumidifying module). In yet a further embodiment, the active material can be a consumable or a fixed deactivating material unit may be provided which can be refilled with the active material. Also, in an embodiment the deactiving material can be a fluid, a powder, or an impregnated solid or may have another form-factor which results in the release of controlled amounts of the deactiving material. Further, in an embodiment the device may include more than one inlet. Alternatively or additionally, the device may include more than one outlet. Further, in an embodiment a device is provided of which the terpene/terpenoid emission is adjustable to the operating environment (volume of the room in which the device is installed, air exchange rate of this room, presence of persons, etc.).

Further, in yet an embodiment a device is provided that may fulfil the following requirements: the volatile organic components that are emitted at ambient conditions (23° C., 50% RH) consist for at least 95 wt. %, more especially at least 97 wt. %, even more especially at least 98 wt. %, etc., of terpene compounds without aliphatic double bonds (examples: carvacrol, thymol, menthol, menthone, eucalyptol). In a special embodiment, a device is provided that emits a mixture of volatiles characterized by at least 95 wt. %, more especially at least 97 wt. %, even more especially at least 98 wt. %, etc., of terpene compounds without aliphatic double bonds. The remaining material may e.g. include compounds with aliphatic double bonds.

Further, the device (and/or system) can optionally be extended with one or more of the following items: (i) several sensors that are coupled to an actuator, controlling automatically the operation of the device (this includes sensors for parameters such as: the level of $CO_2$, Volatile Organic Components, specific VOC's like terpenes or human originating VOC's, levels of air-borne particles, levels or air-borne bacteria, levels of air-borne viruses; (ii) a clock and/or timer function for a time-based adjustment of the device operation; (iii) a light sensor to adjust device operation to light intensity; (iv) an acoustic sensor to adjust device operation to ambient noise levels or specific sounds (e.g. coughing persons); (v) modules that remove air-borne particles such as particle filters (HEPA, HEPA-like, ESP-based filters); (vi) modules to remove unwanted volatile species from air (activated carbon filters, zeolite filters, photo catalytic modules, low temperature catalysts etc. etc. etc.); (vii) modules to increase the air humidity; (viii) modules to reduce the air humidity; (ix) modules that enable remote control (with a dedicated remote control unit or with a cell phone or with Internet control); (x) a maintenance indicator, signaling when terpene module must be re-filled or replaced; (xi) a module that closes inlet and/or outlet; (xii) re-chargeable batteries, solar cells or other energy source enabling operation without connection to the mains, etc. Further, the device and/or system may include a temperature sensor (see also above).

With the invention, it appears that with unexpected low concentrations of terpene comprising deactivating material it is possible to deactivate airborne biological material such as viruses and bacteria, while also maintain the generation of UFP and undesired chemicals like formaldehyde low. Hence, with concentrations (well) below governmental guidelines of terpenes (and possible conversion products), such biological material can be deactivated. This can only be obtained when the specific deactivating material as described herein is used. Also competitor air treatment devices or (de)odorizing devices were tested. It appeared that the balance of low terpene level, low formaldehyde level, low UFP level, and deactivation percentage, was substantially the best for the device (and system) of the invention, while using the herein specified deactivation material.

Hence, the invention provides an air treatment device and/or air treatment system which emits a terpene, which device may (in operation) fulfils one or more of the following requirements: (i) even during long-term operation in a closed room (such as e.g. a 50 $m^3$ room, preferably even in a closed 25 $m^3$ room), the resultant atmosphere fulfils the following air quality guidelines: (ia) the terpene/terpenoid concentrations remain below 1 mg/$m^3$) and especially below 650 μg/$m^3$; (ib) the UFP level remain below the value characteristic for clean air (<4000/$cm^3$), more especially below 1000/$cm^3$, and (ic) formaldehyde level remain below 100 μg/$m^3$, and especially below 30 μgr/$m^3$, especially below a level of 10 μg/$m^3$; (ii) it reduces the levels of air-borne bacteria, such as reducing the level of Colony Forming Units of *Staphylococcus epidermis* (SE) with at least 10%; and it reduces the levels of air-borne viruses, such as reducing the level of Colony Forming Units of MS2 phage with at least 10%. A deactivation (in a space) with 10% of these biological species may already be achieved within about 0.5-2 h with the device and deactivation material as described herein. In this way, the air can at least partly be purified from active biological (airborne) species. Hence, the air treatment device may in embodiment also be applied as air purification device.

The term "substantially" herein, such as in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

BRIEF DESCRIPTION OF THE DRAWINGS

Embodiments of the invention will now be described, by way of example only, with reference to the accompanying schematic drawings in which corresponding reference symbols indicate corresponding parts, and in which.

The schematic drawings are not necessarily on scale.

DETAILED DESCRIPTION OF EMBODIMENTS

Figure 1A:
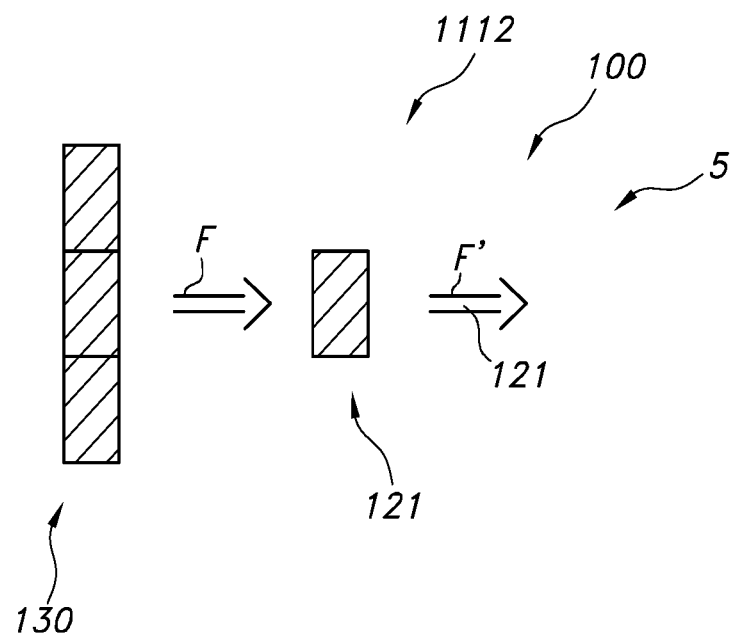
FIGS. 1a-1j schematically depict some aspects of the invention.

FIG. 1a schematically depicts an air treatment device 100 configured to deactivate biological species, such as especially one or more of bacteria and viruses from air. The atmosphere or space from which these may be deactivated is indicated with reference 5. The device 100 comprises a deactivating material 121 comprising for at least 80 wt. % of one or more of a terpene and a terpenoid (both further also indicated as "terpene" or "terpenes") having no aliphatic unsaturated bond. The air treatment device 100 further comprises a gas flow generation device 130. The air treatment device 100 is especially configured to provide said deactivating material 121 into a space with an emission rate S of at maximum 250 mg/h from a release area 1112. Reference F indicates the gas flow generated by the gas flow generation device 130; reference F' indicates the gas flow comprising said deactivating material 121.

FIGS. 1*b*-1*e* schematically depicts some other variants. Here, the device 100 comprises in most variants a device chamber 102 with an inlet opening 111 and an outlet opening 112. The air treatment device 100 is in operation configured to comprise the deactivating material 121 at least partially enclosed by the device chamber 102, wherein the gas flow generation device 130 is configured to introduce air from the space via the inlet opening 111 into the device chamber 102 and to transport at least part of the deactivating material 121 with the air via the outlet opening 112 into the space. Further, the air treatment device 100 is configured to provide said deactivating material 121 into the space with an emission rate S of at maximum 250 mg/h from said outlet opening 112. Reference 120 indicates a deactivating material cartridge. Reference 140 indicates a deactivating material unit (herein also indicated as "active material enclosure"), wherein the deactivating material 121 may be arranged, such a in the form of a cartridge 120 comprising said deactivating material 121. The deactivating material unit 140 may comprise an opening 143. This opening 143 may be in direct fluid contact with the device chamber 102, as shown in FIGS. 1*b* and 1*c*, or may be arranged external from the chamber 102, such as schematically depicted in FIGS. 1*d* and 1*e*. FIGS. 1*a*-1*e*, but also FIGS. 1*f*-1*i* do not show e.g. a heater. Emission of the deactivating material may amongst others be controlled by the gas flow generation device 130 and/or by a heater (or heating unit). For control of the emission solely via the gas flow generation device 130, especially the embodiments of FIGS. 1*b* and 1*c* may be suitable. However, other embodiments than depicted may also be applied. The deactivating material 121 may especially be entrained by the gas flow F/F', especially either already within the air treatment device (see FIGS. 1*b* and 1*c* (and 1*e*)) and/or in the gas flow generated in the space (see FIGS. 1*d* and 1*e*). In FIG. 1*d* (and also 1*e*) the deactivating material 121 can be considered to be associated (at least partly) with an external part of the air treatment device 100. FIGS. 1*f*-1*g* schematically depict variants with a plurality of release areas 1112, such as a plurality of openings 112, with the latter variant extensions, such as tubes, e.g. to serve different spaces, such as different rooms. However, the release areas 1112 may also be arranged in the same space, such as a large room, or a hall, etc.

FIG. 1*h* schematically depicts an air treatment system 1000 comprising i) the air treatment device 100 (without further details) according to any one of the preceding claims and ii) a control unit 1010 configured to control the emission rate S. further, such system 1000 may include one or more sensors 1020, e.g. configured to sense one or more of i) a concentration of a component in air of the deactivating material 121 in a space, ii) an ultra fine particles concentration in air in a space, iii) a conversion product concentration in a space, and iv) another physical or chemical parameter in said space, and wherein the control unit 1010 is configured to control the emission rate S as function of a sensor signal of said sensor 1020 and a corresponding predetermined value for one or more of said component, said ultra fine particles, said conversion product, and said physical or chemical parameter. FIG. 1*i* schematically depicts such device 100 or system 1000 for application for a space 5. FIG. 1*j* is elucidated below. One or more of the sensor 1020 and the control unit 1010 may be integrated in the air treatment device 100 but may also be configured external of the air treatment device 100.

It appears that terpene materials that are used may create UFP's and formaldehyde because of reactions with ambient ozone. This is not desired. Hence, the present invention especially focus on those terpenese that surprisingly show a substantially lower formation of one or more of such species. Very few reports focus on terpenes/terpenoids that do not react with ozone and therefore do not form such potentially hazardous products.

During the last 15 years, extensive work took place to quantify exposure risks from Volatile Organic Components (VOC's) in ambient air. Both Chinese and WHO issued guidelines for formaldehyde levels while Germany issued guidelines for monocyclic and bicyclic terpenes/terpenoids.

It appears that with the present device and deactivating material such guidelines can be met, while nevertheless have the above indicated advantages in relation to deactivating bacteria and virusses. In a specific embodiment, the device described herein is configured to emit non-reactive monocyclic terpenes.

The risks of UFP's or the concern about the health consequences of exposures to high UFP levelsare known in the art. Although UFP guidelines are not yet issued, UFP levels are commonly classified using typical UFP levels in nature, metropolitan and industrial environments. UFP levels are considered acceptable when remaining at levels that occur in clean natural/indoor environments:

| Type | UFP levels [1/cm$^3$] |
|---|---|
| Clean air in the alps | <1.000 |
| Clean office air | 2.000-4.000 |
| Outside Air in urban area | 10.000-20.000 |
| Polluted outside air (smog) | >50.000 |
| Cigarette smoke | >50.000 |
| Workplaces (like welding) | 100.000-1.000.000 |

Until the appearance of guideline values that are applicable to UFP's generated by terpenes/terpenoids, UFP levels of 4.000/cm$^3$ and lower are considered to be acceptable. Hence, especially the device and system are configured and/or can be controlled to keep UFP levels below 10.000/cm$^3$, more especially, even more especially below 4.000/cm$^3$. To this end, a sensor may be used to sence the level of UFP in the relevant space, such as a room in a house or an office space. Especially, UFP is defined as (air-borne) particulate matter of nanoscale size, especially less than 100 nanometres in diameter (or equivalent diameter in the case of a non-spherical particle, i.e. the diameter which would be obtained when the particle with the same volume would be a spherical particle).

However, in the course of the present invention it was found that terpene emitting devices can de-activate effectively bacteria and viruses while still fulfilling the air quality guidelines for terpenes, formaldehyde while maintaining UFP values to levels encountered in clean air or even very clean air.

Hence, especially the invention provides a device that is able to emit controlled low levels of a terpenes/terpenoids at levels such as terpene/terpenoid ≤1 mg/m$^3$, like ≤0.6 mg/m$^3$, especially like ≤0.2 mg/m$^3$. Especially, a terpene is used that does not react with ozone. Further, especially the device is configured and the terpene is selected to de-activate bacteria and/or viruses with each independently more than 10% according to the tests which were executed. Especially, a device may be provided that—while especially fulfilling one or more of the conditions as defined above may optionally generate (or induce generation of) UFP and/or formaldehyde at levels occurring in clean natural/indoor air or far below the indoor air quality guidelines. For instance, the UFP level may especially remain below values characteristic for clean air (<4000/cm$^3$), more especially below about 1000/cm$^3$. Further, especially the formaldehyde level may remain below a values of about 100 μg/m$^3$, and especially below a level of 30 μg/m$^3$, especially below a level of 10 μg/m$^3$.

Figure 1B:
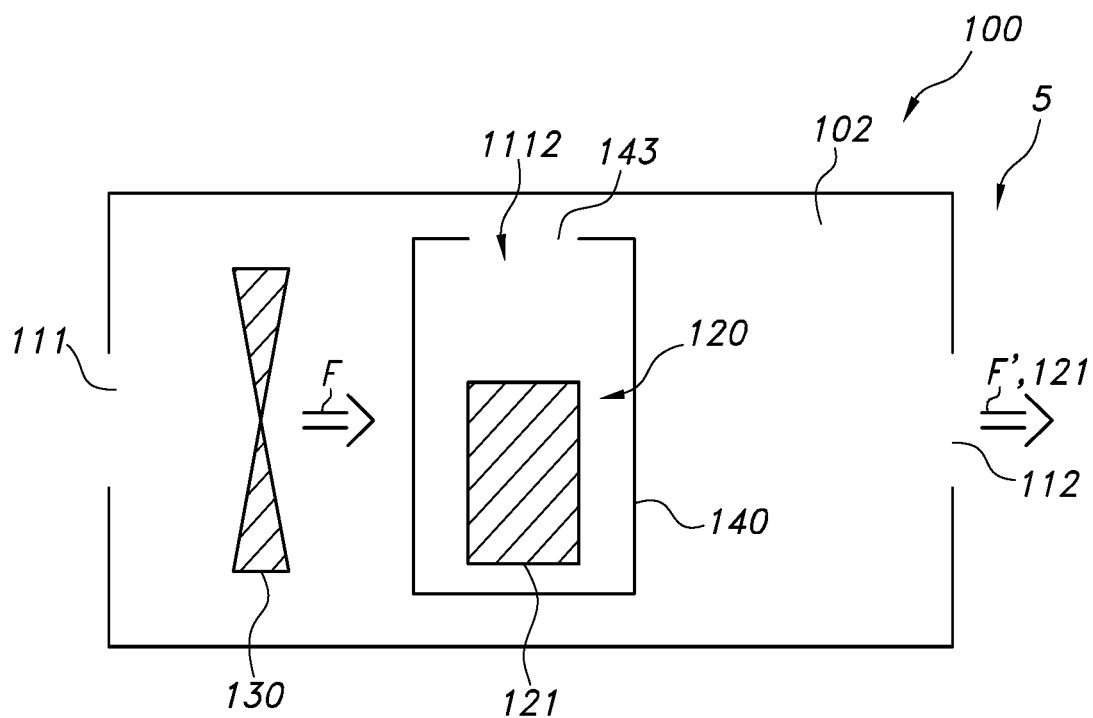
Figure 1C:
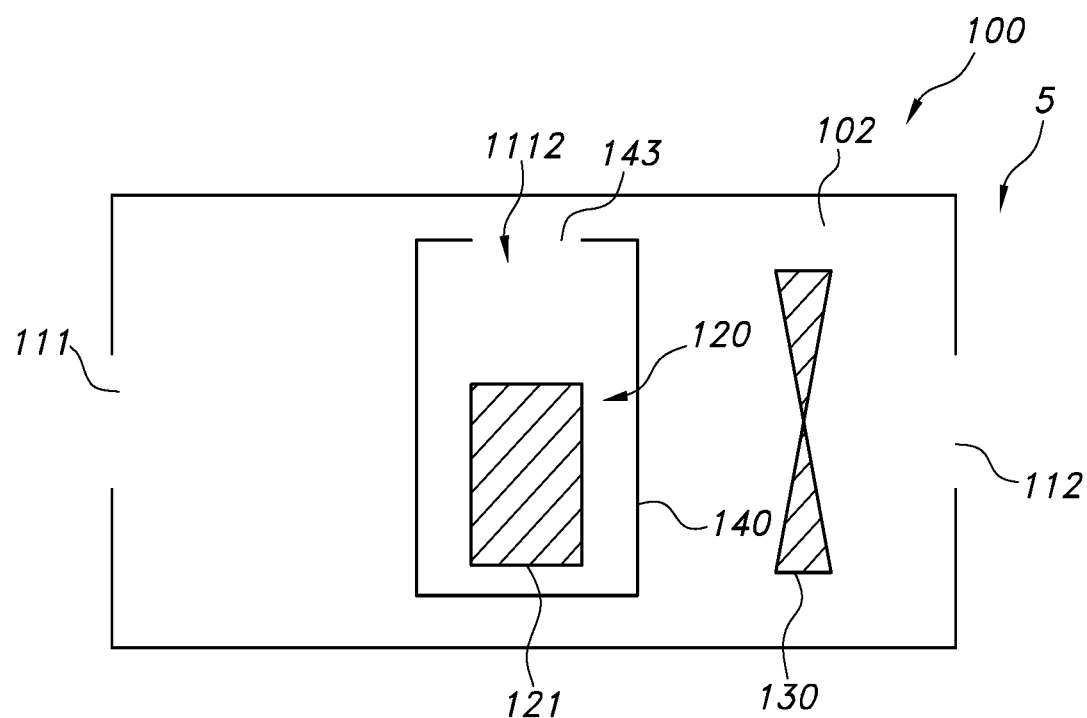
Figure 1D:
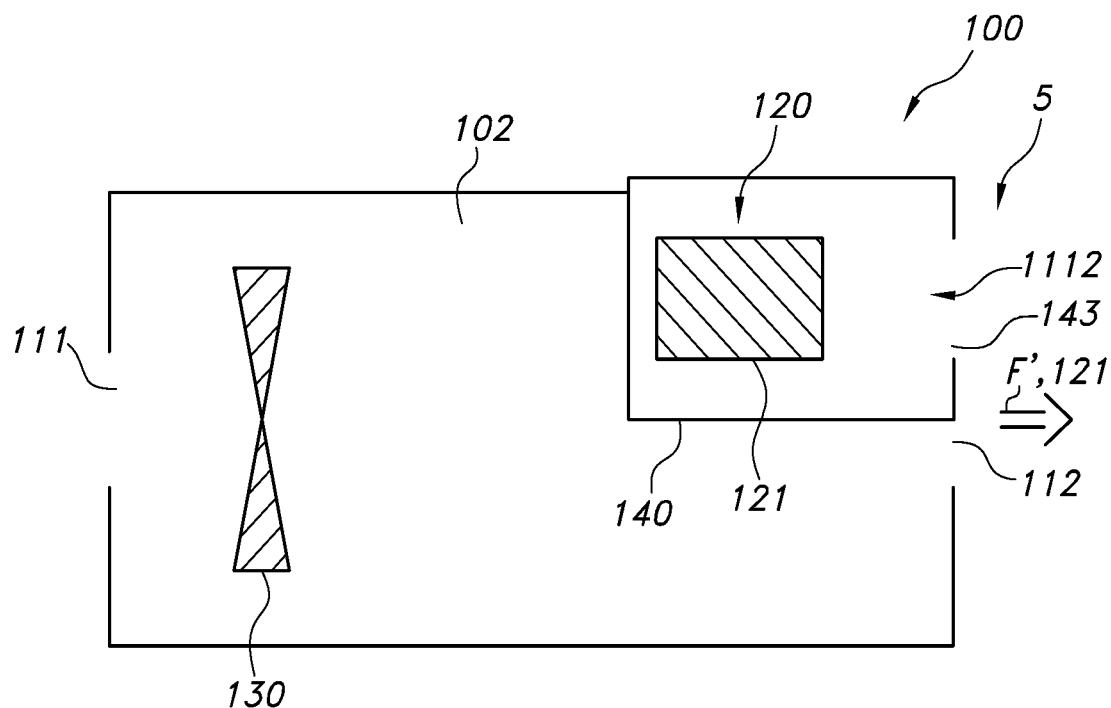
Figure 1E:
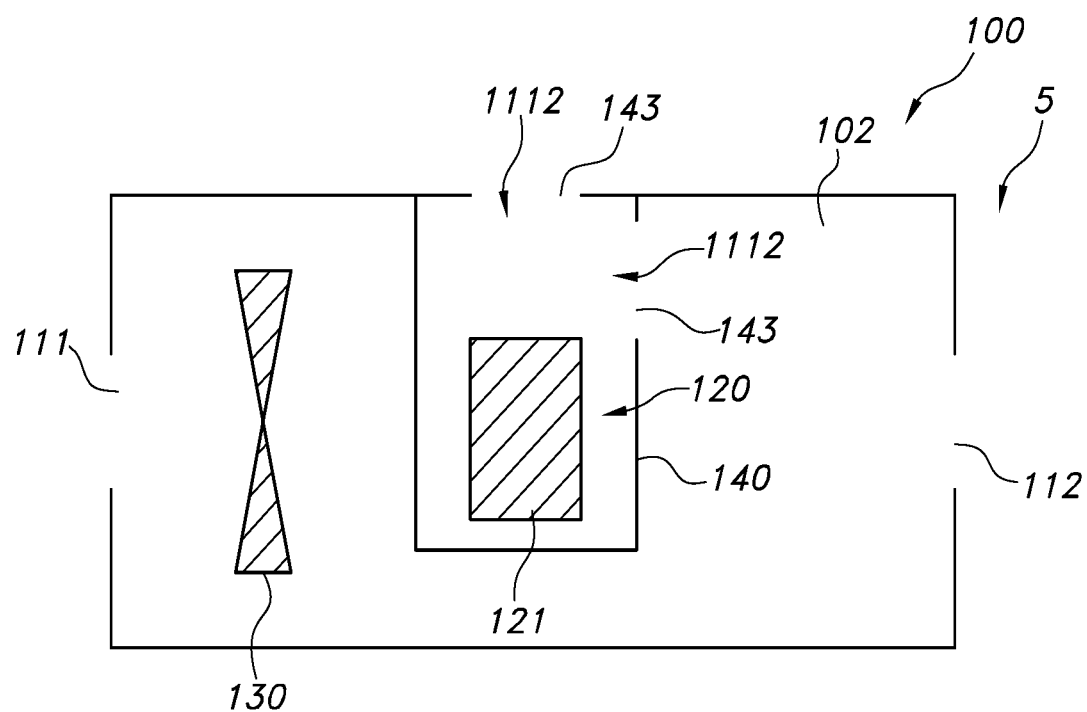
Figure 1F:
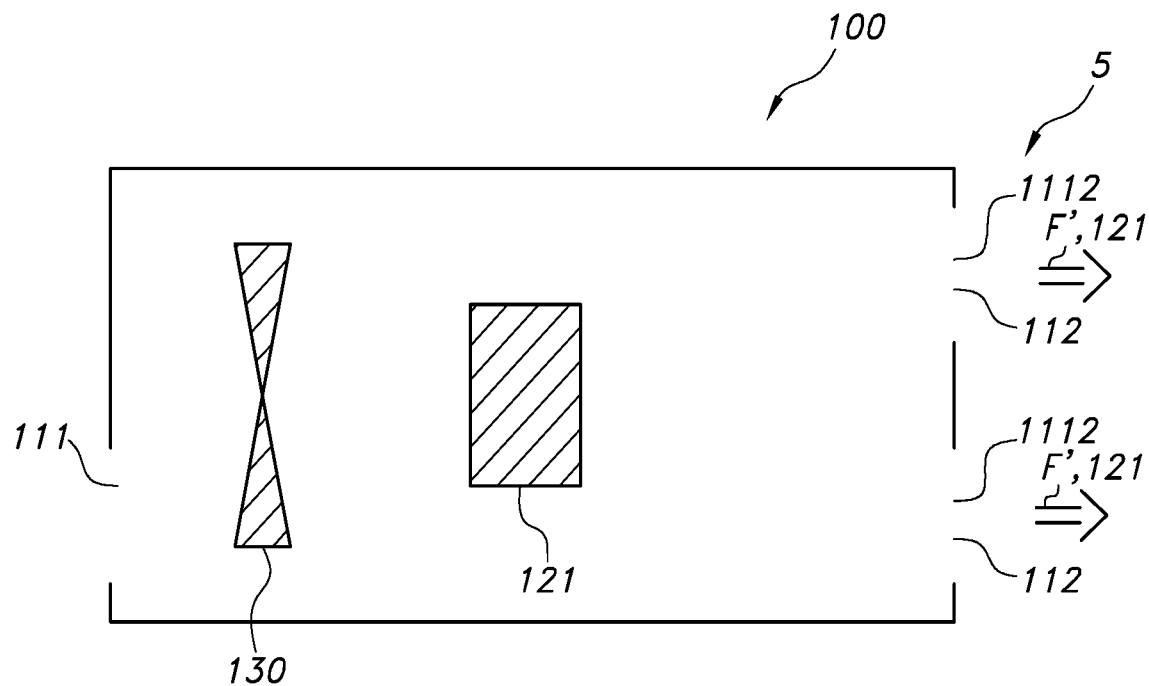
Figure 1G:
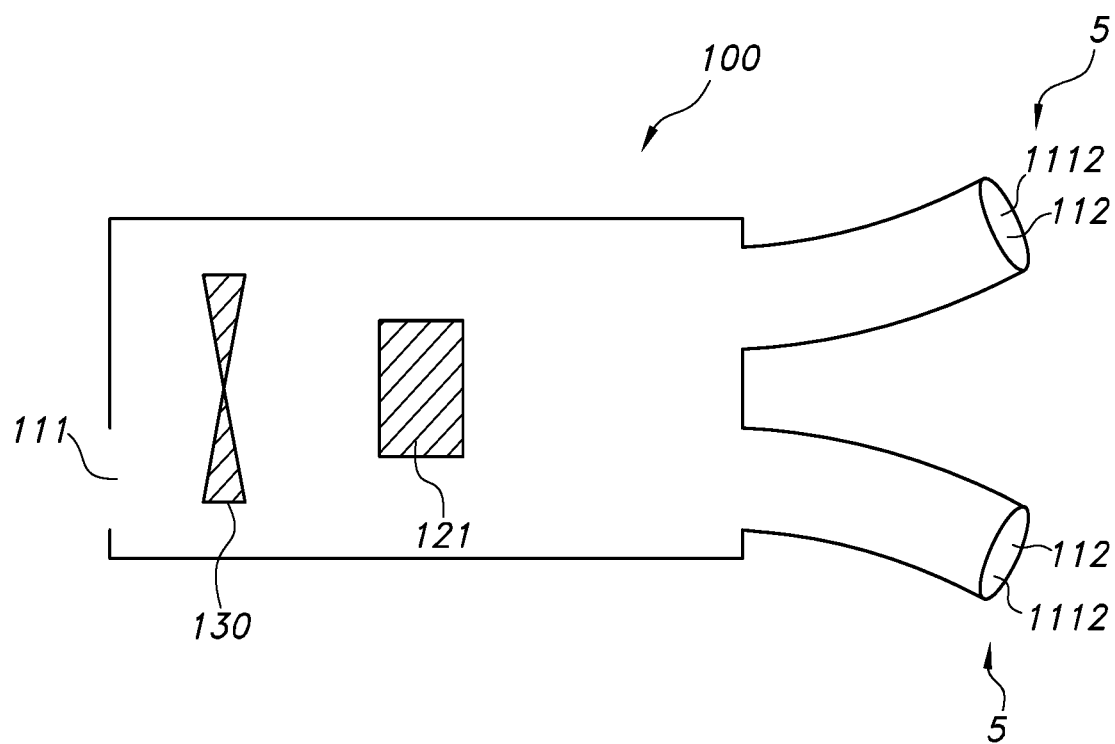
Figure 1H:
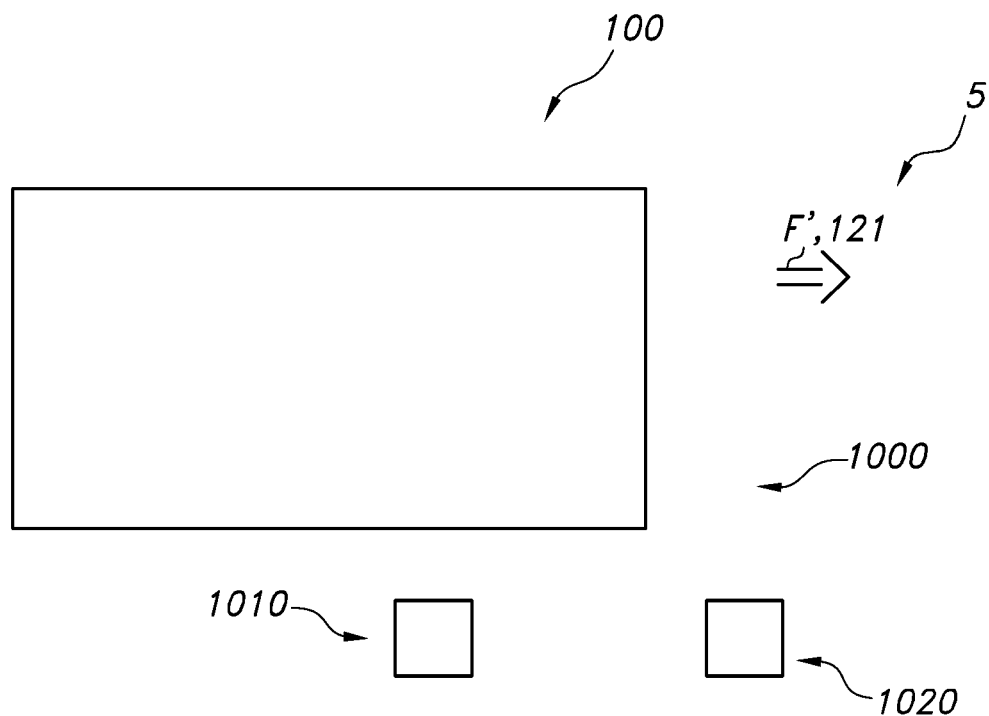
Figure 1I:
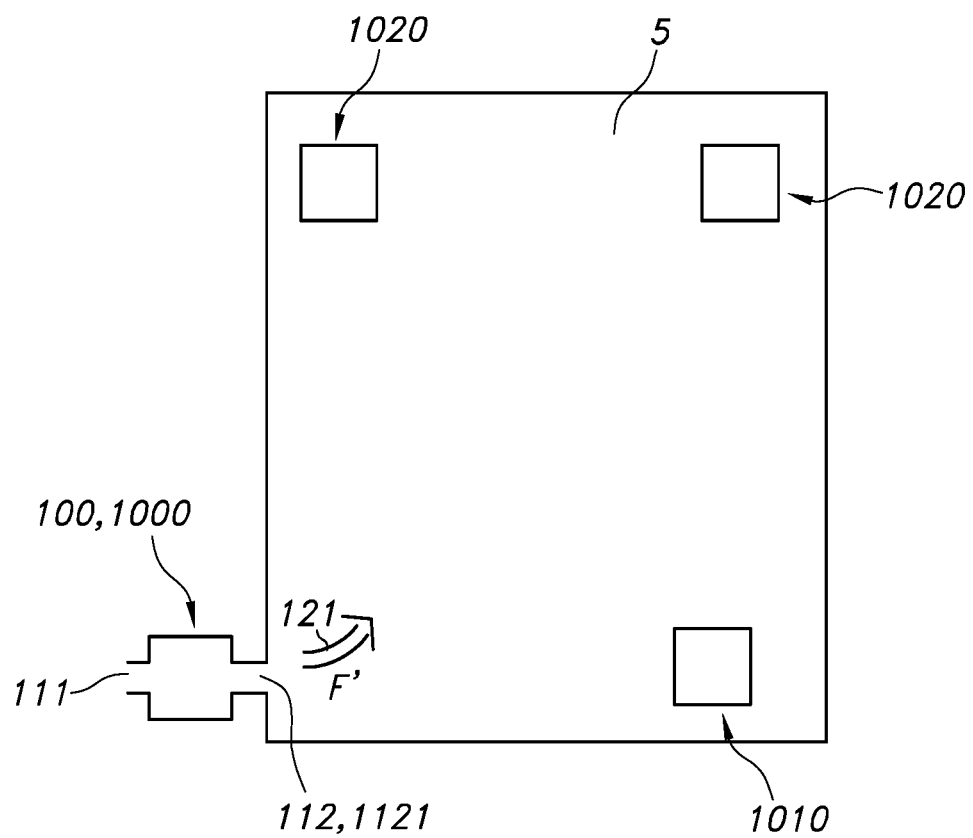

Test were carried out with a basic device 100 which contains a fan as gas flow generation device 130, housing inlet or inlet opening 111 and housing outlet or outlet opening 112, as described in FIG. 1b. The device used in our tests contained an enclosure or deactivating material unit 140, that, in the experiments, included 2 mL of a liquid that consists one or more terpene and/or terpenoid compounds.

In alternative measurements, tests were performed with the basic device that contains a cartridge with two small holes and filled with paper that was impregnated with 2 mL of a mixture of 75 wt % eucalyptol and 25 wt % thymol (Eucalyptol: Sigma Aldrich 99% purity, product code C80601; Thymol: Sigma Aldrich >99.5% purity, product code T0501).

Experiment 1

The device was operated in a 1 m$^3$ box with an air exchange rate of 1.5 hr$^{-1}$ that was ventilated with purified air with and without the addition of approx. 60 ppb which equals 120 μg/m$^3$ ozone. The following items were analyzed at the outlet of the chamber: total VOC content, concentration levels of individual VOC's, levels of formaldehyde and other aldehydes, ozone levels, and UFP levels.

In the absence of ozone, eucalyptol and thymol contents at the outlet were approx. 670 and 6 μg/m$^3$ as measured with Tenax/GC-MS techniques which, considering the air exchange rate of the test chamber, corresponds to hourly evaporation rates of 1000 and 10 μg/hr, respectively. The lower thymol levels agrees with the lower volatility of thymol (as demonstrated by higher boiling points: Eucalyptol: 176-177° C. thymol: 232° C.). It appeared that at least about 96 wt. % of the emitted VOC's (especially defined as C1-C16) consist of eucalyptol and thymol and less than about 4 wt. % of the emitted volatile compounds consistes of very volatile VOC's (<C6). The emitted VOC's contain less than 1% of reactive terpenes (α-pinene and β-pinene). Hence, less than 20 wt. %, especially less than about 1 wt. % of the deactivating material, that is proliferated in air, comprises terpenes with aliphatic double bonds. In the presence of 120 μg/m$^3$ ozone, formaldehyde is formed at 3-4 μg/m$^3$ which is far below some current guideline values, even below average outdoor concentrations. Simultaneously, in the presence of ozone, UFP levels increase with values below 1000 l/cm$^3$ which are also measured in very clean air. The observed small increase of formaldehyde and UFP is tentatively attributed to the low level of reactive terpenes in the eucalyptol/thymol mixture.

From the data studied, it appeared that the creation of undesired side-products can be controlled at very low levels if high purity non-reactive terpenes/terpenoids are used. Note that low levels of side-products were detected even while high eucalyptol/thymol levels were created. In fact, even at such high eucalyptol/thymol levels, the created levels of undesired side-products are below the minimum detection limits of most analytical devices and the formaldehyde/UFP increase will not be noted in household environments because of the typically much higher background levels and the large variations of these background values as caused by human activities and outdoor air quality variations.

Experiment 2

Further, the impact of using low-purity i.s.o. high-purity terpene/terpenoid materials. In this test, the cartridge was loaded with 2 mL of 75/25 wt %/wt % mixture of eucalyptol and thymol. The same thymol was used as above. However, in this case a low-purity eucalyptol sample of natural origin was used. It was found that many types of terpenes/terpenoids were emitted besides eucalyptol. Eucalyptol accounted for less than 25% of the total emitted terpenes/terpenoids. The remaining 75% contains reactive terpenes such as limonene, α-terpinene, terpinolene, α-pinene that may react with ozone to a.o. UFP's. The total level of emitted VOC levels was approx. 3 times higher than in the above experiment. Further, in the presence of 120 µg/m$^3$ ozone, UFP levels increase to above 150.000/cm$^3$ which is 2-3 orders of magnitude higher than found in the above first experiment.

Detailed analysis showed that, in the presence of ozone, levels decrease of reactive terpenes like α-terpinene, terpinolene and limonene and levels increase of acetone, formic acid, acetic acid. Formaldehyde is formed at 20 µg/m$^3$, approx. 5 times higher than in the first experiment. Hence, surprisingly the use of low-purity terpene/terpenoid materials like essential oils can result in the formation of UFP's and side products to levels that exceed guideline values or values typically occurring in pure outdoor air.

Experiment 3

The effectiveness of the terpenes to de-activate air-borne bacteria and viruses was also determined.

The two experiments were performed using two different bacterial species: (1) *Staphylococcus epidermidis* (ATCC12228) is a gram-positive bacterium that is part of the normal human flora, typically the skin flora, and less commonly the mucosal flora. Although *S. epidermidis* is not usually pathogenic, patients with compromised immune systems are at risk of developing infection and these infections are generally hospital-acquired. *S. epidermidis* is a particular concern for people with catheters or other surgical implants because it is known to cause biofilms that grow on these devices; (2) MS-2 Bacteriophage is an icosahedral, positive-sense single-stranded RNA virus that infects the bacterium *Escherichia coli*. It is commonly used as a surrogate test microorganism for viruses.

Culture preparation: The *Staphylococcus epidermidis* used in the tests was prepared by inoculating 100 ml of sterile Tryptone Soya Broth (Oxoid, UK) with a 0.1 ml aliquot of previously frozen cells (in 40% glycerol). The broth was then incubated at 37° C. for 24 hours and shaken at 100 rpm. After 24 hours incubation the culture is assumed to be at the boundary between the exponential and stationary growth phases. After incubation the culture was centrifuged and re-suspended in sterile ringers solution and 1 ml of this suspension was used in the nebulizer as described below.

The MS-2 bacteriophage was prepared by inoculating 100 ml of tryptone soya broth with an aliquot of a pure culture of *E. coli*. The culture was incubated until the culture until reached the exponential growth phase this has been estimated to take around 8 hours at 37° C. Incubating at a lower temperature overnight may achieve the same growth phase. The absorbance of the culture was measured at 600 nm in order to determine if log growth has been achieved—an OD600 of between 0.5-1.0 has been suggested as indicative of log phase growth. Once the culture was in log phase growth it was inoculated with the MS2 phage culture and put back into the shaking incubator until cell lysis occurred—this has be suggested to be as little as 30 minutes or as long as 18 hours. Once cell lysis occurred the culture was centrifuged at 10,000-15,000 g for 15 minutes and the supernatant containing the phage was removed. This supernatant containing the MS-2 phage was used in the nebulizer as described in the following section.

Experimental methodology: the experiments were carried out in the aerobiological test chamber, which consists of a 32.25 m$^3$ hermetically sealed negatively pressurised chamber in which the air flow rate, temperature and relative humidity can be constantly controlled and monitored. The experiments were carried out with the ventilation system set at 1.5 AC/hr (air cycles per hour) at ambient temperature (approx 20° C.) and relative humidity (approx 50%). This means that 1.5*volume of test chamber is supplied every hour. During the microbiological experiments the bacterial aerosols were generated using a 6-jet Collison nebuliser operating at a flow rate of 12 l/min and at a pressure of 20 psi. This was connected to the room via a 25 mm diameter pipe which terminated in a plastic sphere containing twenty four 3 mm diameter holes through which the aerosol was dispersed. Air samples were collected through a plastic pipe located immediately in front of the extract grille. This pipe was connected to a six stage Andersen sampler loaded with sterile agar plates. During the sampling process air passed through the sampler and the bacteria were deposited onto the agar plates. The sampling time was varied depending upon the concentration of the bacterial culture with the aim of collecting between 200 and 300 colony forming units on the agar plates. During the experimental period the temperature, relative humidity and negative/positive ion concentrations were also monitored for 20 minute periods during the control periods and 30 minutes during the device testing periods. Readings were taken every 0.5 seconds and the data used to determine the mean value over a 1 minute period and this is plotted on the graphs in the results section.

The test procedure: In this set of experiments two different types of test procedure were used depending upon the device that was being tested. The first procedure was a first standard testing procedure and the second was an extended test developed in house. The main difference in the test procedure was the amount of time allowed for the device to operate before the test samples were taken. In the standard first test procedure this is 30 minutes and in the extended inhouse test procedure this was 2 hours. When a terpene device had been used the chamber was vented at maximum ventilation rate for 2 hours between tests to ensure that no residual terpene remained in the air inside the chamber.

Figure 1J:
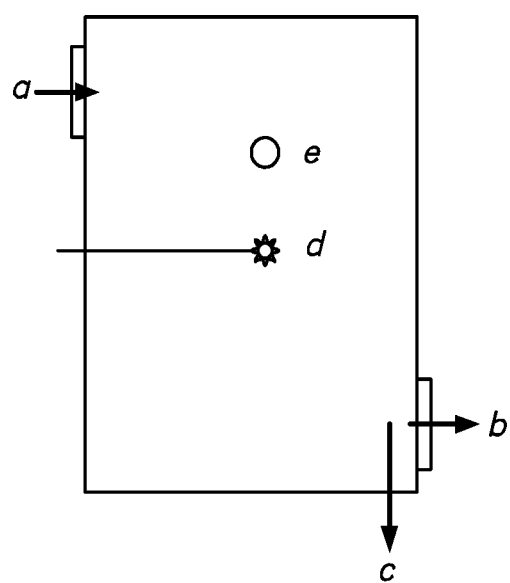

The test room was set up as shown in FIG. 1*j* prior to the start of each experimental run and the chamber door closed and locked and both the sampling port (c) and the nebuliser port (d) sealed. Reference a indicates an air inlet; reference b indicates an air outlet; reference c indicates a sampling port or sampling point; reference d indicates the point at which the bacterial/fungal aerosol is introduced, i.e. the nebuliser port; and reference e indicates the location of the device (as described herein).

Air fans were then switched on and operated at maximum speed (approx 12 AC/hr) for 30 minutes in order to ensure the chamber was sterile. The air fans create the air-flow of 1.5 AC/hr. These fans (located outside the test chamber, similar to all equipment that control temperature (T) and relative humidity (% RH) in the test chamber) are not shown in FIG. 1j. During this purging period the test device remained switched off. During the initial purging period the pre-sterilised nebuliser was prepared and filled with 100 ml of bacterial/phage suspension at a concentration of approximately $10^5$ organisms/ml of sterile distilled water. The nebuliser was then connected to the inlet tube ready for the start of the experiment. In both test procedures after the initial purging period the ventilation rate was reduced to 1.5 AC/hr and nebulisation of the bacterial culture then began and the concentration in the test chamber was allowed to stabilize again. A total of ten samples were then taken at approximately 3 minute intervals during which time the device remained switched off and these are the control samples. During the whole experimental period the temperature and relative humidity was measured.

The agar plates were incubated at 37° C. for 24 hours after which the number of colonies on each plate were counted. All the counts were then subjected to positive hole correction in order to account for multiple impaction. The corrected counts for each set of plates (stages 5 and 6) were added together to give a total count and multiplied to give a count per $m^3$ of test chamber air. Each set of samples represents ten replicates taken during steady state, the first five being the concentration without the device and the second with the device. The mean was taken of the ten replicate samples to give a mean concentration with and without the device. This allowed the mean reduction in concentration to be calculated used to give an indication as to the efficacy of the device.

In order to determine the statistical significance of the results a t-test was carried out on the data sets (Control and Test Period). The purpose of the test is to determine whether the means of the two data sets are statistically different from each other. The test yields a p-value and the smaller the p-value the less likely the difference between the two data sets is the result of chance.

Two replicate experiments were carried out using the basic device without the deactivating material (another material with terpenes was used, not complying with the herein defined conditions) as defined herein, a reference measurement, and with deactivating material as defined herein against aerosols of MS2 bacteriophage. A cfu/$m^3$ reduction in the range of 20.2-25.9% was found.

Also the effect of the basic apparatus, again with a reference measurement and with the deactivation material as defined herein, on aerosols of S. epidermidis was measured. The data showed that the concentration in cfu/$m^3$ was reduced with of 22.4%.

In a further evaluation it appeared that deactivating material not according to the invention may include relatively large amounts of d-limonene, α-pinene and camphene, of which the first two react with ozone to generate small amounts of UFP's and formaldehyde (further information can be provided on request).

Experiment 4

In this experiment, also data from the other experiments described herein are included. Three deactivating materials were tested: (1) eucalyptol (99%)+thymol (99.5%) in a weight ration 3:1, (2) a material comprising 40% limonene including other terpenes, including ozone reactive species; and (3) an eucalyptol (25%) and other terpenes, including ozone reactive species. The following results were obtained in a number of experiments, with e.g. different amounts of starting materials (hence, ranges are given):

| | Terpene/ terpenoid level (mg/$m^3$) | UFP level (/$cm^3$) | Formaldehyde level (μg/$m^3$) | S. epidermidis deactivation (%) | MS-2 deactivation (%) |
|---|---|---|---|---|---|
| eucalyptol (99%) + thymol (99.5%) in a weight ration 3:1 | 0.12-0.72 | <1000 | <2 | 14-43 | 12-29 |
| 40% limonene including other terpenes, including ozone reactive species | 0.1-0.3 | 50,000 | 6 | 22 | 23 |
| eucalyptol (25%) and other terpenes, including ozone reactive species | 2.6 | 150,000 | 20 | n.m. | n.m. |

It appears that the deactivating material as defined herein provides the best balance in results. It further appears that high purity non-reactive terpenes de-activate bacteria and viruses effectively while fulfilling air quality standards and creating low if any additional amounts of nano-particles. In the table, "n.m." indicates not measured; these were not measured as it was clear that the amount of side products, especially double bond containing terpenes (and the possible concomitant undesired reaction products) would be much too high).

Experiment 5

Below some conditions are given for different deactivation materials/deactivating material components, for different rooms. It is assumed that the device will operate in the following conditions:

Room volume: V $m^3$

Ventilation rate: Q dimensionless, (Q is the total hourly air volume that enters the room via ventilations, expressed as a fraction of the room volume)

This means, in a 100 $m^3$ room with ventilation factor=0.25, every hour 25 $m^3$ air enters the room via ventilation.

In normal closed household rooms, ventilation factors below 0.25 are rarely observed.

With windows open, the ventilation rate can increased to above 10, meaning that 1000+$m^3$ of air enter the room every hour by ventilation Terpene emission strength S: mg/h The terpene levels increase to steady state concentration $C_{ss}$ that is characterized by:

$S = Q*V*C_{ss}$ or $C_{ss} = S/(Q*V)$

| Type | Css (mg/m³) | V (m³) | Q (dimensionless) | S (mg/h) |
|---|---|---|---|---|
| Monocyclic terpene | 1 | 25 | 0.5 | 12.5 |
| Monocyclic terpene | 1 | 50 | 0.5 | 25 |
| Monocyclic terpene | 1 | 100 | 0.5 | 50 |
| Monocyclic terpene | 1 | 200 | 0.5 | 100 |
| Bicyclic terpene | 0.2 | 25 | 0.5 | 2.5 |
| Bicyclic terpene | 0.2 | 50 | 0.5 | 5 |
| Bicyclic terpene | 0.2 | 100 | 0.5 | 10 |
| Bicyclic terpene | 0.2 | 200 | 0.5 | 20 |

Assume the device does not specify a minimum room size, e.g. cartridges that emit more than 25 mg/h may create too high terpene levels in rooms of consumer homes. Most especially, terpene emission rates should remain below 25 mg/h, even more especially below 12.5 mg/h in order to generate also acceptable terpene levels in closed rooms of 50 and even 25 m³, respectively. If hourly evaporation rate of the device exceeds 250 mg/h, measures may have to be taken in most of the rooms or other spaces.

In an embodiment, the device may specify a minimum room size in which it should be operated (at this moment not observed at the market). In this case, the cartridge emission rate may e.g. be below $0.5*V_{min}$ with $V_{min}$ equaling the recommended minimum room size of the device.

It is especially desired that 20 wt. % or less of the emitted deactivation material consists of terpenes/terpenoids with reactive aliphatic double bonds. Further, it is especially desired that total of mono-terpene and terpenoid levels in the absence of ozone are in total below 1 mg/m³, especially below 0.2 mg/m³ for bicyclic terpenes. Further, especially the UFP levels in the outlet of the 1 m³ box remain below 10.000/cm³, more especially below 4000/cm³, yet even more especially below 1000/cm³ when operating in the presence of 100 μg/m³ ozone. Further, especially the formaldehyde levels in the outlet of the 1 m³ box remain below 10 μg/m³ when operating in the presence of 100 μgr/m³ ozone.

Experiment 6

Some further measurements were done with setups as describe above. Data in relation to particle generation and ozone consumption as function of type of terpene were determined.

The table below shows nanoparticle levels formed in a 26.5 m³ test chamber, with terpene concentrations of approx. 1 mg/m³ and with an initial ozone concentration of 100 ppb ozone. It is clear that carvacrol, eucalyptol, etc., show best performance.

The table also shows the reduction of ozone levels as a result of generating a terpene concentration of 1 mg/m³ within the 26.5 m³ test chamber. It is clear that e.g. eucalyptol and thymol is most desired amongst these four options.

The following data were obtained:

| Terpene | average O₃ consumption | Particle yield in 10⁶/mol | O₃ max. Error in % |
|---|---|---|---|
| 36 wt % menthol + 64 wt. % menthone | 2% | 391.2 | 76% |
| Thymol | 2% | 498.2 | 70% |
| Eucalyptol | 2% | 779.9 | 66% |
| Carvacrol | 0% | 851.8 | 14% |
| Eugenol | 15% | 18742.9 | 19% |
| Geraniol (not depicted) | 54% | 57608.1 | 13% |
| Linalool | 44% | 76911.2 | 11% |
| Limonene | 31% | 94003.4 | 15% |
| y-terpinene | 19% | 112499.9 | 14% |

The invention claimed is:

1. An air treatment device configured to deactivate one or more of bacteria and viruses from air, the device comprising a deactivating material comprising for at least 80 wt. % of one or more of a terpene and a terpenoid having no aliphatic unsaturated bond,
   the air treatment device comprising:
   a gas flow generation device configured to control the emission of said deactivating material into a space, wherein the deactivating material is entrained by a gas flow generated by the gas flow generation device within the air treatment device,
   a device chamber with an inlet opening and an outlet opening, the air treatment device in operation configured to comprise the deactivating material at least partially enclosed by the device chamber,
   a deactivating material unit situated within the device chamber, configured to host the deactivating material, the deactivating material unit comprising an opening in direct fluid contact with the device chamber,
   wherein the air treatment device is configured to provide said deactivating material into said space with an emission rate (S) of at maximum 250 mg/h from a release area.

2. The air treatment device according to claim 1, wherein the gas flow generation device is configured to introduce air from the space via the inlet opening into the device chamber and to transport at least part of the deactivating material with the air via the outlet opening into the space, wherein the air treatment device is configured to provide said deactivating material into the space with an emission rate (S) of at maximum 250 mg/h from said outlet opening.

3. The air treatment device according to claim 1, wherein the deactivating material comprises for at least 95 wt. % of one or more of a terpene and a terpenoid having no aliphatic unsaturated bond, wherein the deactivating material has a boiling point selected from the range of 150-300° C. or has a boiling point range at least partly overlapping with said range of 150-300° C., and wherein the deactivating material comprises one or more of eucalyptol (1,8-cineol) and thymol.

4. The air treatment device according to claim 1, complying with one or more of the following conditions (i) having a controllable emission rate (S) and (ii) wherein the air treatment device is limited at an emission rate (S) selected from the range of 0.5-50 mg/h from said release area.

5. The air treatment device according to claim 1, comprising a plurality of release areas, wherein the air treatment device is configured to provide said deactivating material into the space with said emission rate (S) from each of said release areas.

6. The air treatment device according to claim 1, wherein the deactivating material unit is configured as refillable unit, and wherein the deactivating material is comprised by a deactivating material cartridge.

7. The air treatment device according to claim 1, wherein the gas flow generation device comprises an ionic wind generator.

8. The air treatment device according to claim 1, wherein the deactivating material comprises for at least 90 wt. % of one or more of a terpene and a terpenoid having no aliphatic unsaturated bond.

9. The air treatment device according to claim 1, wherein the deactivating material comprises for at least 98 wt. % of one or more of a terpene and a terpenoid having no aliphatic unsaturated bond.

10. An air treatment system comprising:
(i) an air treatment device configured to deactivate one or more of bacteria and viruses from air,
the device comprising a deactivating material comprising for at least 80 wt. % of one or more of a terpene and a terpenoid having no aliphatic unsaturated bond,
the air treatment device further comprising:
a gas flow generation device configured to control the emission of said deactivating material into a space, wherein the deactivating material is entrained by a gas flow generated by the gas flow generation device within the air treatment device,
a device chamber with an inlet opening and an outlet opening, the air treatment device in operation configured to comprise the deactivating material at least partially enclosed by the device chamber,
a deactivating material unit situated within the device chamber, configured to host the deactivating material, the deactivating material unit comprising an opening in direct fluid contact with the device chamber,
wherein the air treatment device is configured to provide said deactivating material into said space with an emission rate (S) of at maximum 250 mg/h from a release area, and
(ii) a control unit configured to control the emission rate (S).

11. The air treatment system according to claim 10, configured to maintain a concentration of the deactivating material in air in the space at a level selected from the range of 0.001-1 mg/m$^3$.

12. The air treatment system according to claim 10, further comprising a sensor configured to sense one or more of (i) a concentration of a component in air of the deactivating material in a space, (ii) an ultra fine particles concentration in air in a space, (iii) a conversion product concentration in a space, and (iv) another physical or chemical parameter in said space, and wherein the control unit is configured to control the emission rate (S) as function of a sensor signal of said sensor and a corresponding predetermined value for one or more of said component, said ultra fine particles, said conversion product, and said physical or chemical parameter.

13. A kit of parts comprising:
(i) an air treatment device configured to deactivate one or more of bacteria and viruses from air, the air treatment device comprising a deactivating material comprising for at least 80 wt. % of one or more of a terpene and a terpenoid having no aliphatic unsaturated bond,
the air treatment device further comprising:
a gas flow generation device configured to control the emission of said deactivating material into a space, wherein the deactivating material is entrained by a gas flow generated by the gas flow generation device within the air treatment device,
a device chamber with an inlet opening and an outlet opening, the air treatment device in operation configured to comprise the deactivating material at least partially enclosed by the device chamber,
a deactivating material unit situated within the device chamber configured to host the deactivating material, the deactivating material unit comprising an opening in direct fluid contact with the device chamber, wherein the deactivating material unit is configured as a refillable unit configured to host one or more of said cartridges, and
wherein the air treatment device is configured to provide said deactivating material into said space with an emission rate (S) of at maximum 250 mg/h from a release area, and
(ii) a plurality of cartridges comprising said deactivating material.

14. The kit of parts according to claim 13, further comprising a control unit configured to control the emission rate (S).

15. A cartridge comprising a deactivating material for use in an air treatment device, the device configured to deactivate one or more of bacteria and viruses from air, the deactivating material comprising at least 80 wt. % of one or more of a terpene and a terpenoid having no aliphatic unsaturated bond,
the air treatment device comprising:
a gas flow generation device configured to control the emission of said deactivating material into a space, wherein the deactivating material is entrained by a gas flow generated by the gas flow generation device within the air treatment device,
a device chamber with an inlet opening and an outlet opening, the air treatment device in operation configured to comprise the deactivating material at least partially enclosed by the device chamber,
a deactivating material unit situated within the device chamber configured to host the deactivating material, the deactivating material unit comprising an opening in direct fluid contact with the device chamber, the deactivating material being at least partially enclosed by the device chamber,
wherein the air treatment device is configured to provide said deactivating material into said space with an emission rate (S) of at maximum 250 mg/h from a release area.

16. The cartridge according to claim 15, wherein the deactivating material comprises for at least 95 wt. % of one or more of said terpenes and terpenoids.

17. The cartridge according to claim 15, wherein the deactivating material comprises for at least 80 wt. % of one or more of Menthol, Isomenthol, Neomenthol, Neoisomenthol, Menthone, Isomenthone, Eucalyptol (1,8-cineol), 1,4-cineol, m-Cymene, p-Cymene, Carvacrol, Thymol, p-Cymen-8-ol, Cuminaldehyde, Cuminylalcohol, Iridoid, and Seco-iridoid.

18. A method for deactivating one or more of bacteria and viruses from air in a closed air space, the method comprising:
providing an air treatment device into said closed air space, wherein said air treatment device includes a device chamber with an inlet opening and an outlet opening, and a deactivating material unit situated within the device chamber configured to host the deactivating material, the deactivating material unit comprising an opening in direct fluid contact with the device chamber, arranging a deactivating material into a deactivating material enclosure partially enclosed by the device chamber of the air treatment device, and activating a gas flow generation unit of the air treatment device to control the emission of said deactivating material into said closed air space with an emission rate of at maximum 250 mg/h from a release area, wherein said activation comprises introducing external air into the device via said inlet opening and transporting at least part of the deactivating material with the air via the outlet opening, wherein said deactivating material comprises at least 80 wt. % of one or more of a terpene and a terpenoid having no aliphatic unsaturated bond, with a concentration of the deactivating material in air in said space at a level selected from the range of 0.001-1 mg/m$^3$.

19. The method, according to claim 18, wherein the deactivating material comprises one or more of Menthol, Isomenthol, Neomenthol, Neoisomenthol, Menthone, Isomenthone, Eucalyptol (1,8-cineol), 1,4-cineol, m-Cymene, p-Cymene, Carvacrol, Thymol, p-Cymen-8-ol, Cuminaldehyde, Cuminylalcohol, Iridoid, and Seco-iridoid.

20. The method according to claim 18, further comprising additionally controlling the emission of said deactivating material into said closed air space via a heater unit.

* * * * *